United States Patent
Arribas et al.

(10) Patent No.: US 12,411,195 B2
(45) Date of Patent: Sep. 9, 2025

(54) SYSTEM AND METHOD FOR IMPROVED FAT SUPPRESSION FOR DIFFUSION WEIGHTED IMAGING IN MAGNETIC RESONANCE IMAGING

(71) Applicant: Wisconsin Alumni Research Foundation, Madison, WI (US)

(72) Inventors: Diego Hernando Arribas, Madison, WI (US); Aidan Tollefson, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 345 days.

(21) Appl. No.: 18/098,539

(22) Filed: Jan. 18, 2023

(65) Prior Publication Data

US 2024/0241203 A1 Jul. 18, 2024

(51) Int. Cl.
G01R 33/56 (2006.01)
A61B 5/055 (2006.01)
G01R 33/385 (2006.01)
G01R 33/561 (2006.01)
G01R 33/563 (2006.01)
G06T 11/00 (2006.01)

(52) U.S. Cl.
CPC .......... G01R 33/5607 (2013.01); A61B 5/055 (2013.01); G01R 33/385 (2013.01); G01R 33/5615 (2013.01); G01R 33/56341 (2013.01); G06T 11/008 (2013.01)

(58) Field of Classification Search
CPC .......... G01R 33/56341; G01R 33/5615; G01R 33/385; G01R 33/5607; A61B 5/055; G06T 11/008
See application file for complete search history.

(56) References Cited

U.S. PATENT DOCUMENTS

| | | | |
|---|---|---|---|
| 2018/0259607 A1* | 9/2018 | Liu | G01R 33/50 |
| 2022/0230310 A1* | 7/2022 | Xie | G06T 7/0012 |
| 2023/0358836 A1* | 11/2023 | Setsompop | G01R 33/385 |

OTHER PUBLICATIONS

Burakiewicz J, Charles-Edwards GD, Goh V, Schaeffter T. Water-fat separation in diffusion-weighted EPI using an IDEAL approach with image navigator. Magn Reson Med. Mar. 2015;73(3):964-72. doi: 10.1002/mrm.25191. Epub Apr. 10, 2014. PMID: 24723244.

(Continued)

*Primary Examiner* — Gregory H Curran
(74) *Attorney, Agent, or Firm* — Quarles & Brady, LLP

(57) ABSTRACT

A system and method are provided for acquiring diffusion weighted imaging (DWI) images of a subject using a magnetic resonance imaging system includes performing a chemical-shift encoded (CSE) prescan of a subject to generate a fat image, a water image, and a $B_0$ field map. The method also includes, for each slice or volume of a desired (DWI) acquisition from the subject, determining shim parameters that improve water signal and suppress fat signal. The method further includes performing the DWI acquisition to acquire DWI data form the subject using the shim parameters and reconstructing DWI images of the subject with suppressed artifacts induced by fat of the subject.

22 Claims, 7 Drawing Sheets

(56) References Cited

OTHER PUBLICATIONS

De Graaf, R. A., Brown, P. B., McIntyre, S., Rothman, D. L., & Nixon, T. W. (2003). Dynamic shim updating (DSU) for multislice signal acquisition. MagneticResonance in Medicine, 49(3), 409-416. https://doi.org/10.1002/mrm.10404.

Engström M, Mårtensson M, Avventi E, Norbeck O, Skare S. Collapsed fat navigators for brain 3D rigid body motion. Magn Reson Imaging. Oct. 2015;33(8):984-91. doi: 10.1016/j.mri.2015.06.014. Epub Jun. 25, 2015. PMID: 26117701.

Grande, F. Del, Santini, F., Herzka, D. A., Aro, M. R., Dean, C. W., Gold, G. E., & Carrino, J. A. (2014). Fat-suppression techniques for 3-T MR imaging of themusculoskeletal system. Radiographics, 34(1), 217-233. https://doi.org/10.1148/rg.341135130.

Haase, A., Frahm, J., Hanicke, W., & Matthaei, D. (1985). 1H NMR chemical shift selective (CHESS) imaging. Physics in Medicine and Biology, 30(4), 341-344.https://doi.org/10.1088/0031-9155/30/4/008.

International Search Report and Written Oppinion for corresponding PCT Application No. PCT/US2024/011769, mailed May 15, 2024, 17 pages.

Islam, H., Law, C. S. W., Weber, K. A., Mackey, S. C., & Glover, G. H. (2019). Dynamic per slice shimming for simultaneous brain and spinal cord fMRI.Magnetic Resonance in Medicine, 81(2), 825-838. https://doi.org/10.1002/mrm.27388.

Jinmin Xu, Nicolas Arango, Congyu Liao, Berkin Bilgic, Zijing Zhang, Lawrence L Wald, Setsompop Kawin, Huafeng Liu, and Jason P Stockmann. Lipid Artifact Removal by Dynamic Shimming (LARDS) with multi-coil B0 shim arrays. Proc. Intl. Soc. Mag. Reson. Med. 29 May 15-20, 2021.

Kun Zhou, Wei Liu, and Yulin V Chang. A TSE BLADE based distortion-free diffusion-weighted imaging method with Dixon water-fat separation. Proceed. of the Internation society for magnetic resonance in medicine, 28th annual meeting and exhibition, Aug. 8-14, 2020. B28, 958, Jul. 24, 2020.

Lee SK, Tan ET, Govenkar A, Hancu I. Dynamic slice-dependent shim and center frequency update in 3 T breast diffusion weighted imaging. Magn Reson Med. May 2014;71(5):1813-8. doi: 10.1002/mrm.24824. Epub Jun. 24, 2013. PMID: 23798360; PMCID: PMC3830606.

Meneses, B. P., & Amadon, A. (2021). A fieldmap-driven few-channel shim coil design for MRI of the human brain. Physics in Medicine and Biology, 66(1).https://doi.org/10.1088/1361-6560/abc810.

Metz, T. (2014). Purpose Theory I. Meaning in Life, 23, 77-97. https://doi.org/10.1093/acprof:oso/9780199599318.003.0005.

Roberts, N. T., Hinshaw, L. A., Colgan, T. J., Ii, T., Hernando, D., & Reeder, S. B. (2021). B0 and B1 inhomogeneities in the liver at 1.5 T and 3.0 T. MagneticResonance in Medicine, 85(4), 2212-2220. https://doi.org/10.1002/mrm.28549.

Sarlls JE, Pierpaoli C, Talagala SL, Luh WM. Robust fat suppression at 3T in high-resolution diffusion-weighted single- shot echo-planar imaging of human brain. Magn Reson Med. Dec. 2011;66(6):1658-65. doi: 10.1002/mrm.22940. Epub May 20, 2011. PMID: 21604298; PMCID: PMC3162087.

Sengupta, S., Welch, E. B., Zhao, Y., Foxall, D., Starewicz, P., Anderson, A. W., Gore, J. C., & Avison, M. J. (2011). Dynamic B0 shimming at 7 T. MagneticResonance Imaging, 29(4), 483-496. https://doi.org/10.1016/j.mri.2011.01.002.

Shi, Y., Vannesjo, S. J., Miller, K. L., & Clare, S. (2018). Template-based field map prediction for rapid whole brain B0 shimming. Magnetic Resonance inMedicine, 80(1), 171-180. https://doi.org/10.1002/mrm.27020.

Stockmann, J. P., & Wald, L. L. (2018). In vivo B0 field shimming methods for MRI at 7 T. NeuroImage, 168, 71-87. https://doi.org/10.1016/j.neuroimage.2017.06.013.

Winfield JM, Douglas NH, deSouza NM, Collins DJ. Phantom for assessment of fat suppression in large field-of-view diffusion-weighted magnetic resonance imaging. Phys Med Biol. May 7, 2014;59(9):2235-48. doi: 10.1088/0031-9155/59/9/2235. Epub Apr. 8, 2014. PMID: 24710825.

Yu H, Shimakawa A, McKenzie CA, Brodsky E, Brittain JH, Reeder SB. Multiecho water-fat separation and simultaneous R2* estimation with multifrequency fat spectrum modeling. Magn Reson Med. Nov. 2008;60(5):1122-34. doi: 10.1002/mrm.21737. PMID: 18956464; PMCID: PMC3070175.

\* cited by examiner

SYSTEM AND METHOD FOR IMPROVED FAT SUPPRESSION FOR DIFFUSION WEIGHTED IMAGING IN MAGNETIC RESONANCE IMAGING

STATEMENT REGARDING FEDERALLY SPONSORED RESEARCH

This invention was made with government support under EB030497 awarded by the National Institutes of Health. The government has certain rights in the invention.

BACKGROUND

The field of the invention is systems and methods for magnetic resonance imaging (MRI). More particularly, the invention relates to systems and methods for improved fat suppression for diffusion weighted imaging in MRI.

When a substance, such as human tissue, is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field, $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, $G_z$) are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

To do so, the signals are often weighted in different ways to give preference to or consider different sub-signals or so-called contrast mechanisms. Two basic "contrast mechanisms" commonly utilized in MR imaging are the spin-lattice (or longitudinal or $T_1$) relaxation time or spin-spin (or transverse or $T_2$) relaxation time. However, there are a variety of other mechanisms for eliciting contrast. For example, diffusion weighting imaging (DWI) is a powerful contrast mechanism that finds clinical application in a wide variety of setting. MRI has the unique ability, as compared to other imaging modalities, to encode the diffusion of water within tissue. Tissues with altered water content or varying cellularity have different levels of quantitative diffusion within tissue. For example, the diffusion of water within acute cerebral ischemia or within highly cellular tumors is known to exhibit more restriction of diffusion. With acquisitions that are weighted by the local diffusion, these tissues exhibit less signal decay than surrounding tissues. This differential signal decay can be encoded into the magnitude of the signal and diffusion-weighted images can be generated as well as quantitative diffusion maps.

Diffusion-based methods rely on the magnitude of the diffusion encoded signal. The magnitude of the diffusion-weighted signal is fit into a signal model thought to represent the underlying physics of the MR signal in a particular tissue (e.g., mono-exponential signal decay). Fat suppression is important in many MR imaging applications, including DWI based on echo-planar imaging, where unsuppressed fat signals appear shifted due to the large chemical shift artifact, and consequently may obscure the organs of interest. Chemical-shift based fat suppression is often used with DWI, but fails in the presence of substantial $B_0$ inhomogeneities. Importantly, chemical shift-based fat suppression failures are common in clinical practice and often lead to non-diagnostic image quality, particularly in the presence of a complex magnetic susceptibility environment, such as the thorax, abdomen, and lower extremities.

Thus, there is a need for improved systems and methods for DWI that reduce the probability of acquiring images that cannot be used for clinical purposes, for example, due to low SNR exacerbated by chemical-shift artifacts.

SUMMARY

The present disclosure overcomes the aforementioned drawbacks by providing systems and methods for acquiring diffusion weighted imaging (DWI) images of a subject with increased water signal and decreased fat signal, thereby increasing clinical utility by decreasing risk of artifacts. In one non-limiting example, shim or imaging parameters for the DWI acquisition can be determined on a slice-by-slice or volume-by-volume basis, using data from a chemical-shift encoded (CSE) acquisition performed before the DWI acquisition.

In accordance with one aspect of the disclosure, a magnetic resonance imaging (MRI) system is provided that includes a magnet system configured to generate a polarizing magnetic field about at least a portion of a subject arranged in the MRI system and a plurality of gradient coils configured to apply magnetic gradients to the polarizing magnetic field. The MRI system also includes a radio frequency (RF) system configured to apply an excitation field to the subject and acquire MR image data from the subject and a computer system. The computer system is programmed to control the plurality of gradient coils and the RF system to perform a chemical shift encoded pre-scan of the subject to acquire CSE data. The computer is further programmed to use the CSE data to predict a water signal and a fat signal across a plurality slices or volumes and select at least one of shim parameters or acquisition parameters for each of the plurality slices or volumes that achieves a desired predicted water signal and fat signal. The computer is also programmed to control the plurality of gradient coils and the RF system to perform a diffusion-weighted imaging (DWI) acquisition to acquire DWI data using each of the at least one of shim parameters or acquisition parameters for each of the plurality slices or volumes that achieves the desired predicted water signal and fat signal. Additionally, the computer is programmed to reconstruct the DWI data to produce an image of the subject with suppressed artifacts induced by fat of the subject.

In accordance with another aspect of the disclosure, a method is provided for acquiring diffusion weighted imaging (DWI) images of a subject using a magnetic resonance imaging system. The method includes performing a chemical-shift encoded (CSE) prescan of a subject to generate a fat image, a water image, and a B0 field map and, for each slice or volume of a desired (DWI) acquisition from the subject, determining shim parameters that improve water signal and suppress fat signal. The method also includes performing the DWI acquisition to acquire DWI data from the subject using the shim parameters and reconstructing DWI images of the subject with suppressed artifacts induced by fat of the subject.

In accordance with yet another aspect of the disclosure, a method is provided for acquiring diffusion weighted imaging (DWI) images of a subject using a magnetic resonance imaging system. The method includes performing a chemical shift encoded pre-scan of the subject to acquire CSE data and, using the CSE data, predicting a water signal and a fat signal across a plurality slices or volumes and selecting at least one of shim parameters or acquisition parameters for each of the plurality slices or volumes that achieves a desired predicted water signal and fat signal. The method further includes performing a diffusion-weighted imaging (DWI) acquisition to acquire DWI data using each of the at least one of shim parameters or acquisition parameters for each of the plurality slices or volumes that achieves the desired predicted water signal and fat signal. Also, the method includes reconstructing the DWI data to produce an image of the subject with suppressed artifacts induced by fat of the subject.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
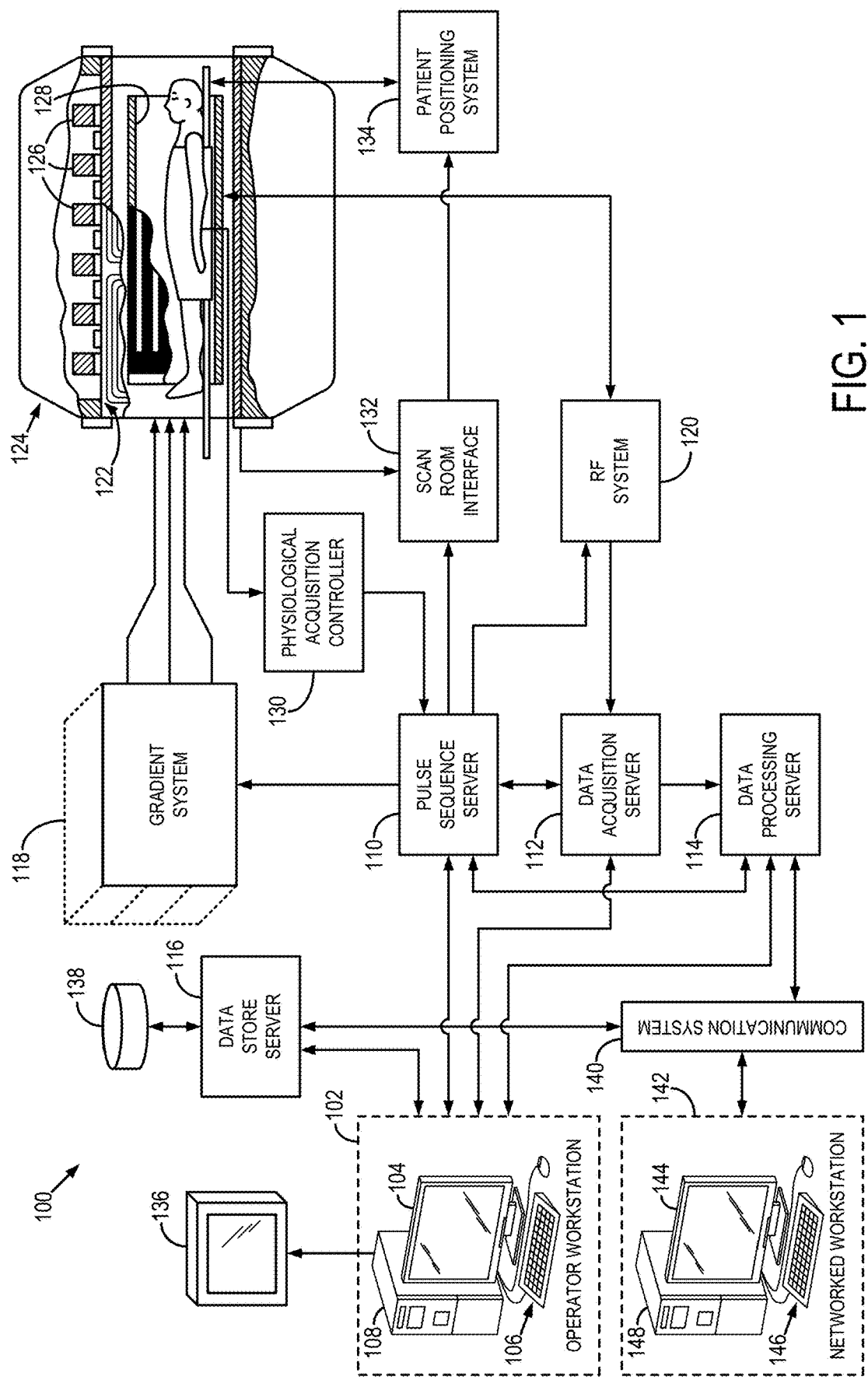
FIG. 1 is a block diagram of an exemplary magnetic resonance imaging ("MRI") system configured in accordance with the present disclosure.

The systems and methods described herein may be implemented using a magnetic resonance imaging (MRI) system 100, such as is illustrated in FIG. 1. The MRI system 100 includes an operator workstation 102, which will typically include a display 104, one or more input devices 106 (such as a keyboard and mouse or the like), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers, including a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radio frequency ("RF") system 120. Gradient waveforms to perform the prescribed scan are produced and applied to the gradient system 118, which excites gradient coils in an assembly 122 to produce the magnetic field gradients $G_x$, $G_y$, $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2};\qquad \text{Eqn. 1}$$

and the phase of the received magnetic resonance signal may also be determined according to the following relationship:

$$\varphi = \tan^{-1}\left(\frac{Q}{I}\right);\qquad \text{Eqn. 2}$$

for positive real values, and $$\varphi = \pi + \tan^{-1}\left(\frac{Q}{I}\right);\qquad \text{Eqn. 3}$$

for negative real values.

The pulse sequence server 110 also optionally receives patient data from a physiological acquisition controller 130.

By way of example, the physiological acquisition controller 130 may receive signals from a number of different sensors connected to the patient, such as electrocardiograph (ECG) signals from electrodes, or respiratory signals from a respiratory bellows or other respiratory monitoring device. Such signals are typically used by the pulse sequence server 110 to synchronize, or "gate," the performance of the scan with the subject's heartbeat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data are lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data are acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction techniques, such as iterative or backprojection reconstruction techniques; applying filters to raw k-space data or to reconstructed images; generating functional magnetic resonance images; calculating motion or flow images; and so on.

Images reconstructed by the data processing server 114 are conveyed back to the operator workstation 102. Images may be output to operator display 104 or a display 136 that is located near the magnet assembly 124 for use by attending clinician. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse or the like), and a processor 148. The networked workstation 142 may be located within the same facility as the operator workstation 102, or in a different facility, such as a different healthcare institution or clinic. The networked workstation 142 may include a mobile device, including phones or tablets.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2:
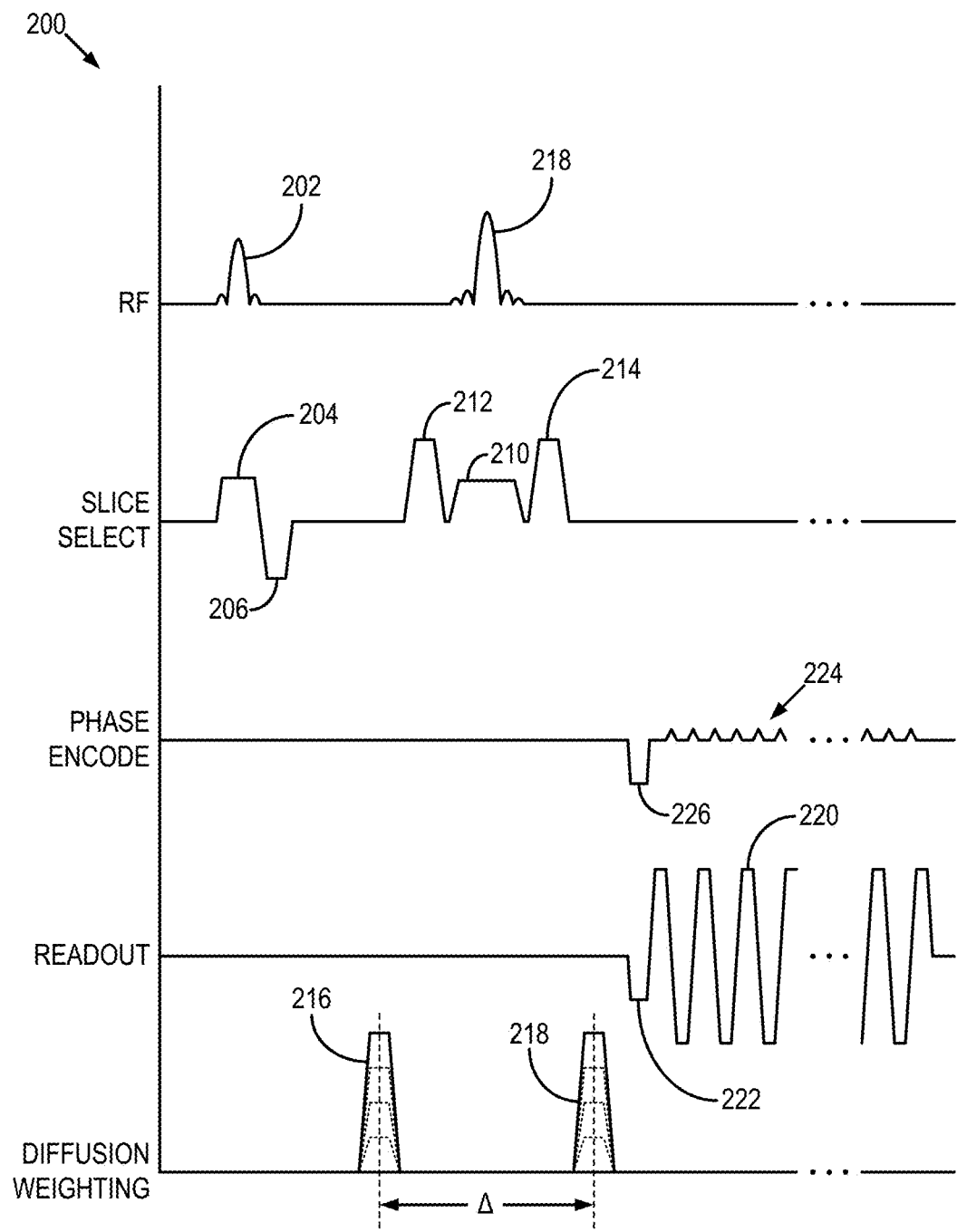
FIG. 2 is a graphic representation of an exemplary pulse sequence for directing the MRI system of FIG. 1.

The above-described MRI system can be used to implement a variety of pulse sequences to effectuate desired imaging studies. One category of pulse sequence is the is the echo-planar imaging (EPI) pulse sequence. One non-limiting example of an EPI pulse sequence 200 is shown in FIG. 2. The pulse sequence 200 includes a radio frequency (RF) excitation pulse 202 that is played out in the presence of a slice-select gradient 204 in order to produce transverse magnetization in a prescribed imaging slice. The slice-select gradient 204 includes a rephasing lobe 206 that acts to rephase unwanted phase dispersions introduced by the slice-select gradient 204, such that signal losses resultant from these phase dispersions are mitigated. Next, a refocusing RF pulse 208 is applied in the presence of another slice-select gradient 210 in order to refocus transverse spin magnetization. In order to reduce unwanted phase dispersions, a first crusher gradient 212 bridges the slice-select gradient 210 with a second crusher gradient 214.

The slice-select gradient 210 and crusher gradients 212 and 214 are further bridged by a first and second diffusion weighting gradient, 216 and 218, respectively. These diffusion weighting gradients 216 and 218 may be equal in size, that is, their areas are equal. The diffusion weighting gradients 216 and 218, while shown on a separate "diffusion weighting" gradient axis, are produced through the application of diffusion weighting gradient lobes along each of the slice-encoding, phase-encoding, and frequency-encoding gradient directions. By changing the amplitudes and other characteristics of the diffusion weighting gradient lobes, the acquired echo signals can be weighted for diffusion occurring along any arbitrary direction. For example, when the diffusion weighting gradients 216 and 218 are composed solely of gradient lobes applied along the $G_z$ gradient axis, the acquired echo signals will be weighted for diffusion occurring along the z-direction. As another example, if the diffusion weighting gradients 216 and 218 are composed of gradient lobes applied along both the $G_x$ and $G_y$ gradient axes, then the echo signals will be weighted for diffusion occurring in the x-y plane along a direction defined by the relative amplitudes of the gradient lobes.

Diffusion weighting of the acquired echo signals is provided when spins undergo random Brownian motion, or diffusion, during the time interval, Δ, spanned between the application of the first and second diffusion gradients 216 and 218, respectively. The first diffusion weighted gradient 216 dephases the spins in the imaging volume, whereas the second diffusion weighted gradient 218 acts to rephase the spins by an equal amount. When spins undergo random diffusive motion during this time interval, however, their phases are not properly rephased by the second diffusion gradient 218. This phase difference results in a signal attenuation related to the diffusion occurring along the direction prescribed by the diffusion weighting gradients 216 and 218. The more diffusion that occurs, the more signal attenuation that results.

Following excitation of the nuclear spins in the prescribed imaging volume, data are acquired by sampling a series of diffusion-weighted echo signals in the presence of an alternating readout gradient 220. The alternating readout gradient 220 may be preceded by the application of a pre-winding gradient 222 that acts to move the first sampling point along the frequency-encoding, or readout, direction by a prescribed distance in k-space. Spatial encoding of the echo signals along a phase-encoding direction is performed by a series of phase encoding gradient steps 224, which are each played out in between the successive signal readouts such that each echo signal is separately phase-encoded. The phase-encoding gradient steps 224 are preceded by the application of a pre-winding gradient 226 that acts to move the first sampling point along the phase-encoding direction by a prescribed distance in k-space. As is known in the art, the foregoing pulse sequence 200 can be repeated a plurality of times while applying a different slice-select gradients 204 and 210 during each repetition such that a plurality of slice locations are sampled.

In combination with acquiring imaging data using an EPI pulse sequence, such as described above, fat suppression techniques may be applied to suppress signal from fat that could result in artifacts in the final images. Unfortunately, traditional fat suppression techniques assume a homogeneous $B_0$ field upon which the gradients are applied. However, very commonly, the $B_0$ field is not homogenous. In this case, the $B_0$ inhomogeneities can lead to failures in fat suppression or water excitation, particularly in complex susceptibility environments. To address any known inhomogeneities in the $B_0$ field, shimming can be performed. However, conventional volumetric shimming methods are frequently unable to compensate for complex $B_0$ inhomogeneities, which leads to residual fat signal and artifacts in the images. This can be particularly problematic when performing DWI in areas of the body that may include substantial fat, such as the abdomen or periphery (less so in the head).

However, unlike traditional fat suppression strategies that apply a fixed gradient shim or a single fat suppression strategy, the systems and methods provided herein can dynamically adjust. This may be performed across the entire region of interest, or performed in a slice-by-slice implementation. Furthermore, the systems and methods provided herein do not treat fat suppression as a concept that is "laid over" the imaging acquisition. Rather, as will be described, the present disclosure provides systems and methods for slice or volume variable (e.g., slice-by-slice) correction and suppression to provide improved DWI. Systems and methods are provided for dynamic shimming using information such as a water-only image, a fat-only image, and $B_0$ field map, derived from a chemical shift-encoded acquisition. With knowledge of the water/fat distributions and $B_0$ field map, the present disclosure provides systems and methods for dynamically adjusting the acquisitions parameters and/or fat suppression parameters, and/or shimming parameters across the acquisition, including slice-by-slice or volume-by-volume.

Figure 3:
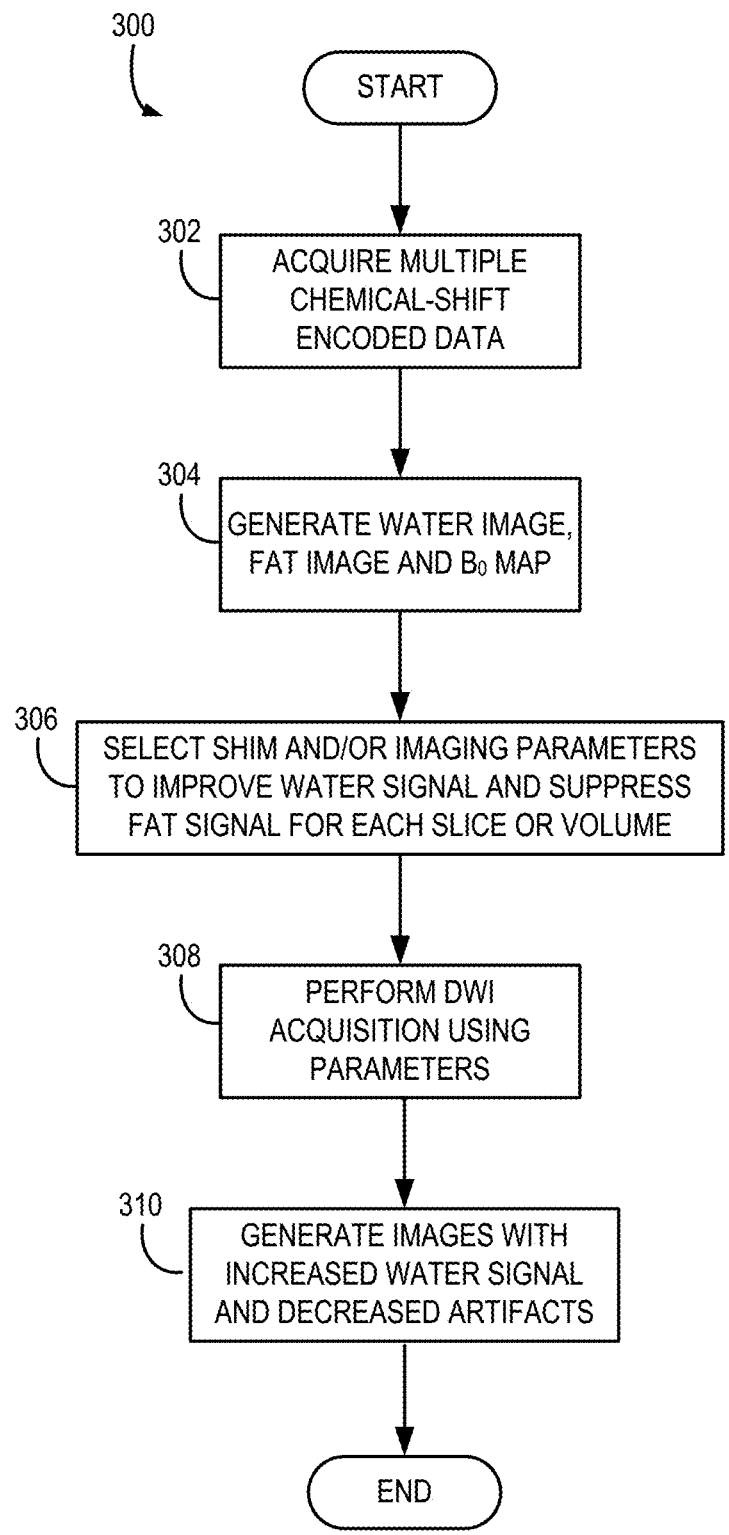
FIG. 3 is a flow chart setting forth some non-limiting example steps of a method in accordance with the present disclosure that may be performed, for example, using the system of FIG. 1.

In particular, referring to FIG. 3, a process 300 in accordance with the present disclosure, which may be implemented using a system such as described with respect to FIG. 1, will be described. The process 300 begins with the acquisition of chemical-shift encoded (CSE) data from a subject at process block 302. This acquisition at process block 302, though not required, may be co-localized with subsequent acquisition of DWI data. From the CSE data, separate water and fat images can be produced, as well as a $B_0$ field map at process block 304. The CSE data can be acquired using a multi-echo acquisition designed for separation of water and fat signals, quantification of fat, as well as quantification of T2* decay (often denoted using the inverse of T2*, ie: R2*=1/T2*). By acquiring images at multiple echo times (TE), the interference between water and fat signals, as well as R2* decay can be used to generate proton density fat fraction (PDFF) and R2* maps. R2* maps can be used to check water-only images to ensure the water images are accurate or not corrupted. CSE-MRI techniques, including those using iterative decomposition of water and fat with echo asymmetry and least-squares estimation (IDEAL) or Dixon methods, can be used to yield at least a fat image, a water image, and a $B_0$ field map, which can be used to perform dynamic fat suppression and imaging acquisitions, as will be described.

Specifically, with patient and slice-specific (or volume-specific) knowledge provided by the fat-only image, water-only image, and $B_0$ field map, the excited water and fat signals throughout the field of view (FOV) can be predicted and shim or acquisition parameters selected to improve signal and reduce artifacts, including those induced by shifts. At process block 306, the known spectral selectivity profile of the DWI excitation is used to identify the desired combination of these shim and/or acquisition parameters to balance water excitation signals and control fat signal excitation. In particular, a selection criteria may be applied to select shim and/or acquisition parameters on a slice-by-slice or volume-by-volume basis.

In one non-limiting example, a selection may predict increase water signals and decrease fat signals throughout the FOV and select "shim" parameters (2 directions+center frequency if working with 2D slices or 3 directions+center frequency if working with 3D volumes) at each slice or volume that correlate with that goal of improving water signal and decreasing fat signal. Additionally or alternatively, imaging parameters may be selected, such as the direction of the EPI readout, the type of spatial-spectral pulse, higher order shims (if available), and/or the use of T1-based fat suppression methods. Furthermore, the selection may use a parameters selection process that is selected based on the region of the subject being imaged. For example, one selection process may be used for a whole-body study and a different selection process may be used for a particular organ, such as the liver.

In the case of a 2D application (in x and y), in one non-limiting example, a selection process may use a balancing criteria, such as follows:

$$(cf', Xshim', Yshim') = \underset{cf, Xshim, Yshim}{\operatorname{argmin}} \sum_{x} \sum_{y} \left| \sum_{p=1}^{6} M_{fat}(x, y) \cdot \right.$$

$$a_{fat,p} \cdot I(\Delta f_{fat,p} + fieldmap(x, y) + Xshim \cdot x + Yshim \cdot y -$$

Eqn. 4

$$cf\bigg|^2 - |M_{water}(x, y) \cdot I(fieldmap(x, y) + Xshim \cdot x + Yshim \cdot y - cf)|^2;$$

where cf is the center frequency and cf' is a calculated, desired center frequency; Xshim is the shim value in the x-direction and Xshim' is a calculated, desired shim value in the x-direction; Yshim is a shim value in the y-direction and Yshim' is calculated, desired shim value in the y-direction; p is one of six fat peak resonances with relative amplitude ($a_{fat,p}$) and frequency offset ($\Delta f_{fat,p}$), center frequency (cf), magnetization ($M_{fat}$), and excitation intensity (I) based on the signal's off-resonance and the known excitation spectral profile; $M_{water}$ is the magnetization of water signal; and field map(x,y) reflects the $B_0$ values in x and y from the $B_0$ field map.

In a clinical setting, the data acquired at process block 302 may be used to generate the information at process block 304 that is then passed to pulse sequence configuration module at process block 306. In this way, the implementation of the steps described with respect to process blocks 302-306 may be automated for a user of an MRI system of FIG. 1. Thus, at process block 308, a DWI acquisition may be performed using the parameters, for example, that may be selected using a balancing criteria, such as the non-limiting example provided in equation 4. Notably, as set forth above, the parameters are selected on a slice-by-slice basis (or volume-by-volume basis).

Figure 4:
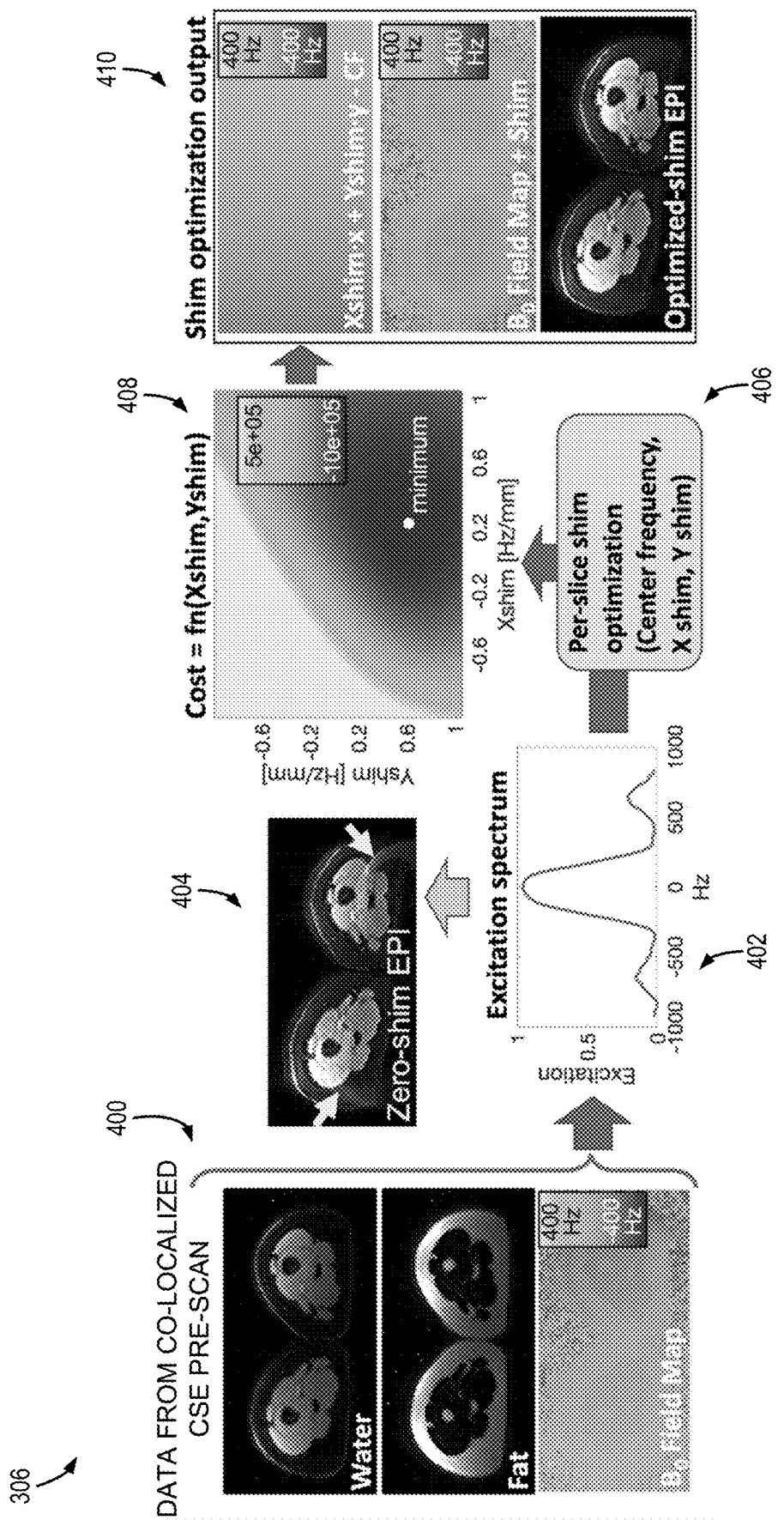
FIG. 4 is a data-flow diagram giving one, non-limiting example of a process based on the steps of FIG. 3.

This process is further illustrated in FIG. 4. That is, the operations of process block 306 is illustrated graphically in FIG. 4. That is, data from the CSE pre-scan 400, which as described above may optionally be co-localized, is used to determine an excitation spectrum 402 that is relative to a zero-shimmed EPI acquisition 404, which yields per-slice shim parameters (cf, Xshim, Yshim) 406. These are evaluated via the selection process 408, which may be embodied as a cost function, such as equation 4, to yield shim and/or imaging acquisition parameters that meet the selection criteria 410. Thus, the maps of excited water and fat intensities are predicted based on the CSE-derived water-only image, fat-only image, $B_0$ field map, in combination with the known spectral excitation profile of the DWI acquisition.

With this, referring again to FIG. 3, the data acquired at process block 308, images of the patient can be generated that reflect increased water signal and decreased artifacts (for example, from fat signal) compared to images acquired using traditional fat suppression.

As variations to the process described above, segmentation may be performed and shimming parameters selected or applied on a segment-by-segment basis. As noted, though a 2D (x-y) example is provided, shimming or imaging in z may be performed. Furthermore, shimming parameters may be selected based on the region of interest. For example, fat signal may be tolerated when it is aligned out of the ROI or a given slice.

Thus, systems and method are provided to leverage CSE-based information to select shimming and/or imaging parameters on a slice-by-slice (or volume-by-volume) basis for DWI imaging, particularly, in applications where fat suppression failures due to $B_0$ inhomogeneity currently remain a frequent source of major artifacts, such as extra-cranial applications for DWI. In a complicated $B_0$ environment where linear shims may not be enough to homogenize the $B_0$ field over the entire slice, the systems and methods provided herein can be adapted to prioritize suppressing regions of fat that would otherwise shift into an organ of interest, such as will be shown below in experimental results.

EXAMPLES

In one study, a phantom comprised of a thin layer of peanut oil resting on a larger volume of water was imaged. A surgical implant was placed near the phantom to induce substantial $B_0$ inhomogeneities. In another study, multiple healthy volunteers (both male and female) were imaged with IRB approval and informed written consent.

Each imaging was performed using a 3 T, GE Signa Premier system. For the human subjects, the acquisitions included axial DWI and 2D CSE scans of the upper leg and abdomen. Abdominal scans used respiratory triggering (DWI) or a single breath-hold (CSE). Acquired series included four co-localized 2D multi-slice acquisitions: a conventional volumetrically shimmed DWI, a DWI with zero shims, a 2D CSE scan, and an optimized-shim DWI. DWI parameters included: 6 mm slice thickness; 10-16 mm spacing to obtain substantial S/I coverage; 15 slices; 4 repetitions; diffusion b-values=100 s/mm2 and 500 s/mm2. The DWI scans included spatial-spectral excitation for water excitation/fat suppression. CSE parameters included: 128× 128 matrix size, TR=7.6 ms, TE1=1.0 ms, dTE=1.0 ms, 6 echoes. From the CSE acquisition we obtained co-localized fat-only and water-only images, B0 field maps, and R2* maps.

Figure 5:
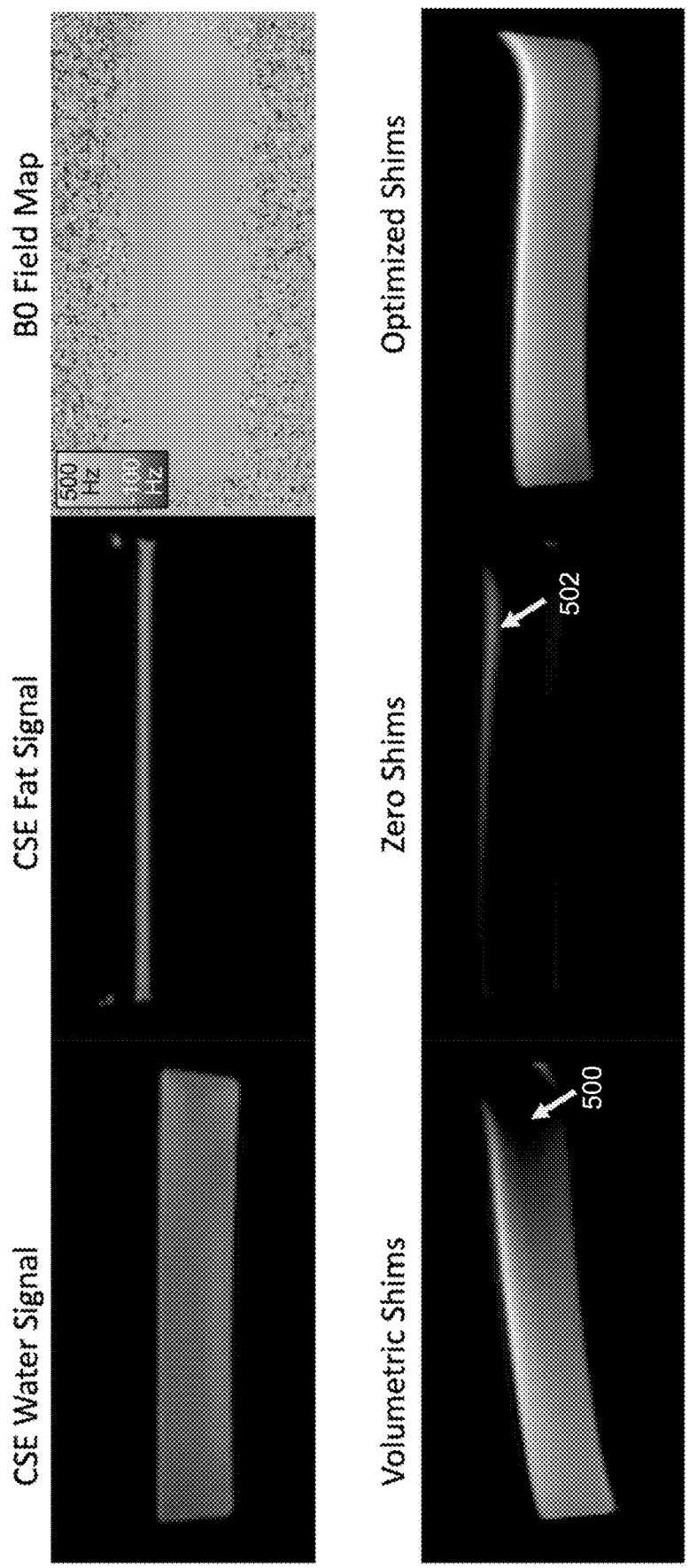
FIG. 5 is a set of correlated images from one study performed using the systems and methods of the present disclosure.

Phantom scans with optimized shims showed decreases in the number and severity of fat suppression failures, as illustrated in FIG. 5. In particular, the phantom DWI scans demonstrate water excitation failure in the volumetric and zero shim cases 500 and fat suppression failure in the zero shim case 502 are improved with optimized shims. The $B_0$ field has been intentionally affected by the presence of a nearby metal surgical implant. The optimized shim case demonstrates better water excitation and reduced fat suppression failure. The CSE-derived water-only and fat-only images are shown in the top row for reference.

Figure 6:
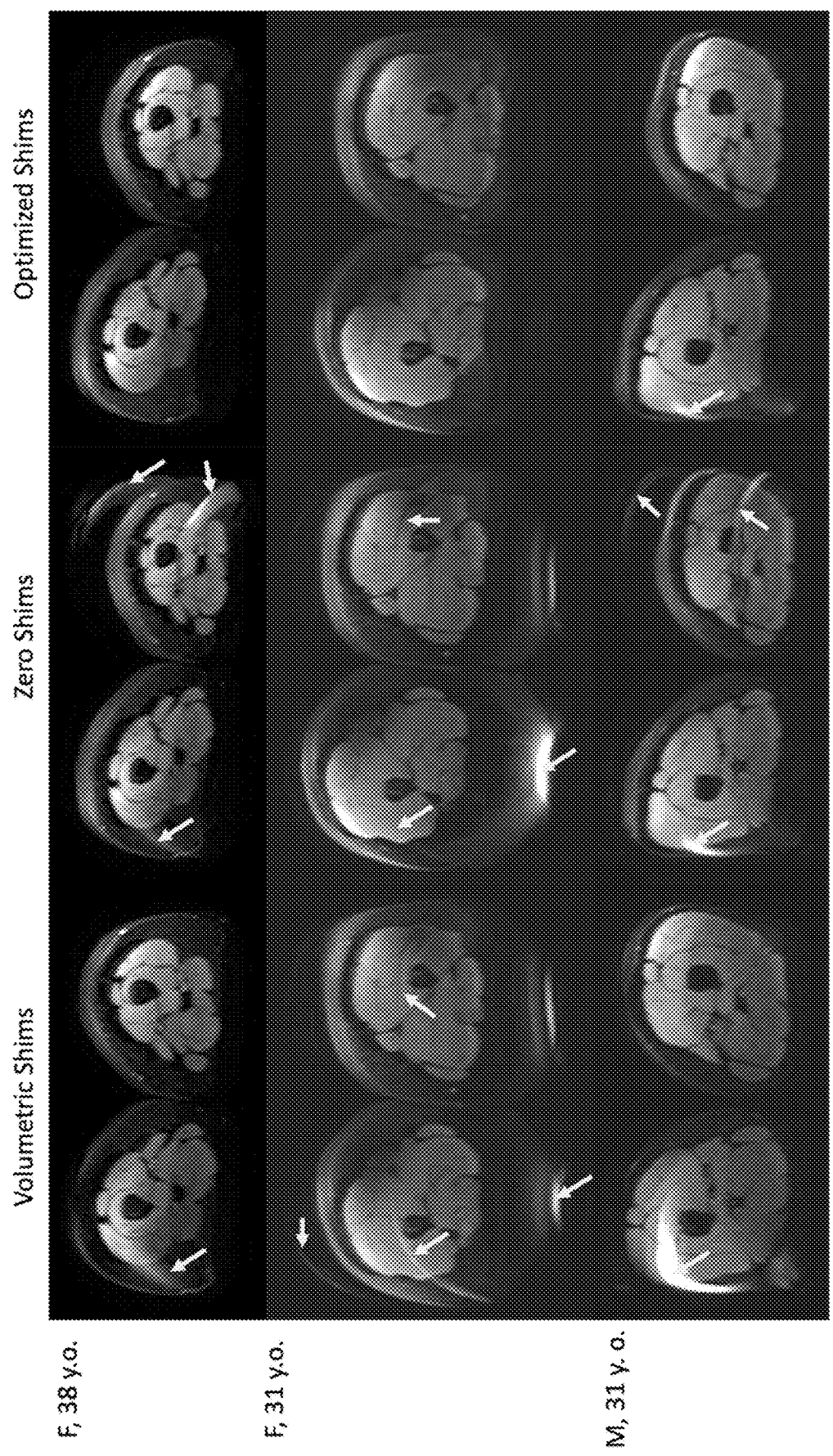
FIG. 6 is a set of images acquired from the periphery of human subjects during another study performed using the systems and methods of the present disclosure.

Upper leg scans regularly demonstrated large fat suppression failures in multiple slices of volumetrically-shimmed DWI scans. These artifacts were minimized using CSE-based slice-specific dynamic shimming optimization, such as illustrated in FIG. 6. More particularly, upper leg scans for three different volunteers showing improved fat suppression in the optimized shim cases. The arrows indicate fat suppression failures. From left to right FIG. 6 shows volumetric shim DWI scans, zero shim DWI scans, optimized shim DWI scans. Female (38) and male (31) volunteers had metal implants below the knee, which perturbed the $B_0$ field. These successful cases demonstrate the robustness of the method to improve DWI quality in tough environments.

Figure 7:
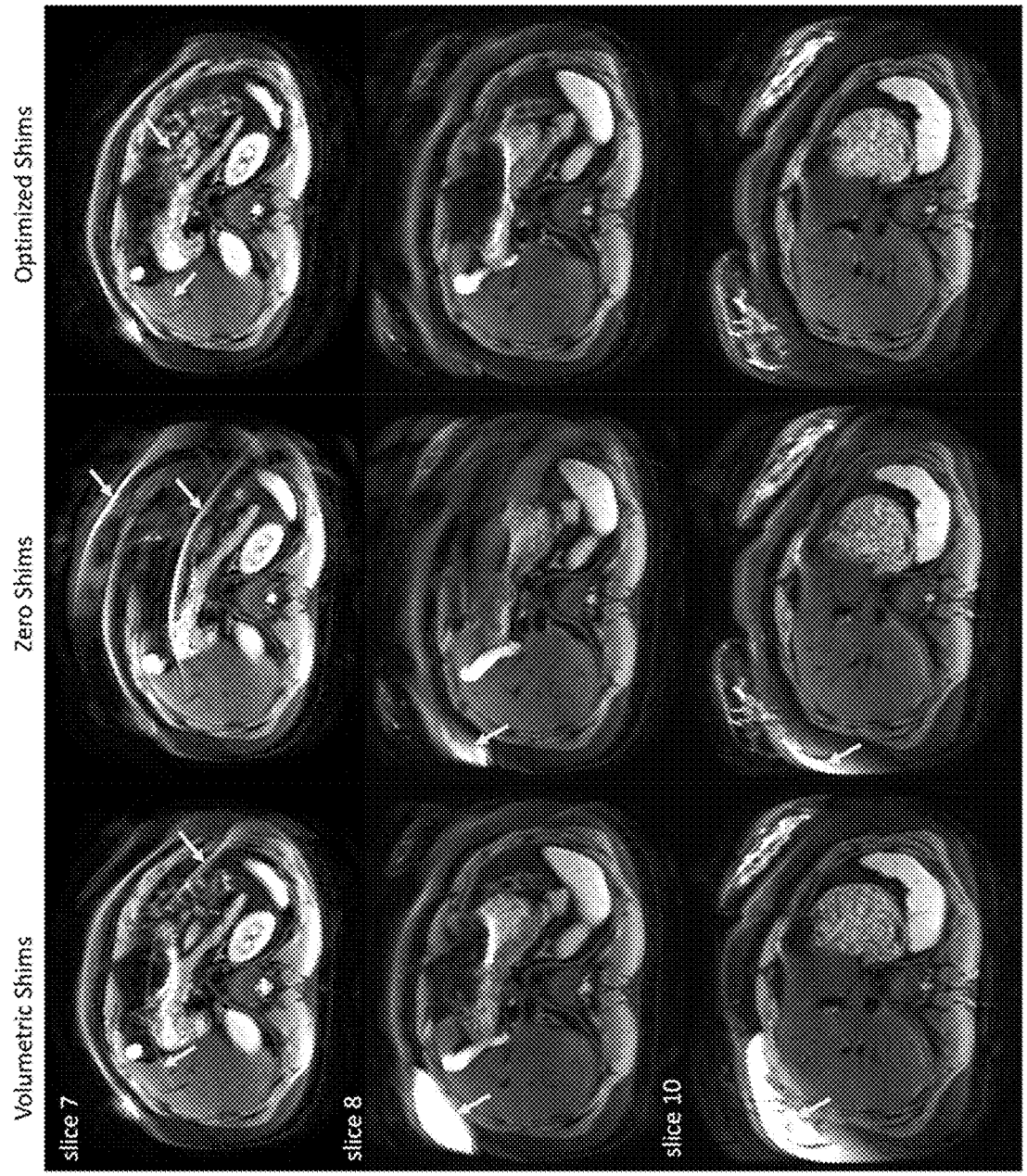
FIG. 7 is a set of images acquired from an abdomen a human subject during another study performed using the systems and methods of the present disclosure.

Further performance improvements were observed in the abdomen, such as illustrated in FIG. 7. That is, FIG. 7 provides multiple abdominal scans for a single volunteer demonstrating improved fat suppression in the optimized shim cases. The arrows indicate fat suppression failures. From left to right, FIG. 7 provides volumetric shim DWI scans, zero shim DWI scans, optimized shim DWI scans.

Thus, systems and methods are provided that can realize an automated process that uses a CSE pre-scan as part of a DWI imaging acquisition to improve DWI, particularly, in extra-cranial applications in the presence of substantial fat depots and complex magnetic field environments, including thorax, abdomen, extremities, and whole-body diffusion MRI. The pre-scan itself is brief and does not add appreciable time-on-table.

More particularly, a rapid chemical shift encoded (CSE)-based "pre-scan" is performed to determine the water/fat distributions and magnetic field map in each desired slice. Then, for each desired slice (such as each slice for a subsequent diffusion EPI series), shim and/or imaging parameters can be determined that desirably change (or even optimize) image quality, based on knowledge of the water/fat distribution and magnetic field map. The determined shims or acquisition parameters are adjusted on a per-slice basis to perform a dynamic shimming and/or dynamic acquisition that yields substantially improved fat suppression and image quality compared to traditional fat suppression for DWI studies.

As used herein in the context of computer implementation, unless otherwise specified or limited, the terms "component," "system," "module," "controller," "framework," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance imaging (MRI) system comprising:
a magnet system configured to generate a polarizing magnetic field about at least a portion of a subject arranged in the MRI system;
a plurality of gradient coils configured to apply magnetic gradients to the polarizing magnetic field;
a radio frequency (RF) system configured to apply an excitation field to the subject and acquire MR image data from the subject;
a computer system programmed to:
control the plurality of gradient coils and the RF system to perform a chemical shift encoded pre-scan of the subject to acquire CSE data;
generate at least a fat-only image, a water-only image, and a B0 field map from the CSE data;
using the water image, the fat image, and the B0 map, predict a water signal and a fat signal across a plurality of slices or volumes and select at least one of shim parameters or acquisition parameters for each of the plurality slices or volumes that achieves a desired predicted water signal and fat signal;
control the plurality of gradient coils and the RF system to perform a diffusion-weighted imaging (DWI) acquisition to acquire DWI data using each of the at least one of shim parameters or acquisition parameters for each of the plurality slices or volumes that achieves the desired predicted water signal and fat signal; and
reconstruct the DWI data to produce an image of the subject with suppressed artifacts induced by fat of the subject.

2. The MRI system of claim 1, wherein performing the DWI acquisition using each of the at least one of shim parameters or acquisition parameters includes dynamically adjusting the at least one of shim parameters or acquisition parameters for each of the plurality slices or volumes.

3. The MRI system of claim 1, wherein selecting at least one of shim parameters or acquisition parameters for each of the plurality slices or volumes includes applying a cost function.

4. The MRI system of claim 3, wherein the cost function optimizes at least one of shim parameters or acquisition parameters on a slice-by-slice or volume-by-volume basis.

5. The MRI system of claim 1, wherein controlling the plurality of gradient coils and the RF system to perform the DWI acquisition includes performing a echo-planar imaging (EPI) pulse sequence.

6. The MRI system of claim 1, wherein the CSE data includes an $R2^*$ map, and wherein the $R2^*$ map is used to generate a water-fat map or the B0 field map, or to select estimates in the water-fat map or B0 field map for use when predicting the water signal and the fat signal across the plurality slices or volumes.

7. The MRI system of claim 1, further comprising selecting a parameter selection function to use to select the at least one of shim parameters or acquisition parameters for each of the plurality slices or volumes based on a region of the subject being imaged.

8. The MRI system of claim 1, wherein selecting at least one of shim parameters or acquisition parameters for each of the plurality slices or volumes includes selecting shim parameters in two directions and relative to a center frequency if the DWI acquisition is to be performed using 2D slices or three directions and relative to a center frequency if the DWI acquisition is to be performed in using 3D volumes.

9. The MRI system of claim 1, wherein selecting at least one of shim parameters or acquisition parameters for each of the plurality slices or volumes includes selecting a direction of readout, a type of spatial-spectral pulse, or a T1-based fat suppression method.

10. The MRI system of claim 1, wherein the shim parameters are applied only during water-selective excitation of the DWI acquisition.

11. The MRI system of claim 1, wherein the shim parameters are applied during an entire duration of the DWI acquisition.

12. A method for acquiring diffusion weighted imaging (DWI) images of a subject using a magnetic resonance imaging system, the method comprising:
performing a chemical-shift encoded (CSE) prescan of a subject to generate a fat image, a water image, and a B0 field map;
for each slice or volume of a desired (DWI) acquisition from the subject, determining shim parameters that improve water signal and suppress fat signal;
performing the DWI acquisition to acquire DWI data form the subject using the shim parameters; and
reconstructing DWI images of the subject with suppressed artifacts induced by fat of the subject.

13. The method of claim 12, further comprising determining parameters for the DWI acquisition that improve water signal and suppress fat signal in the presence of the shim parameters.

14. The method of claim 12, wherein determining the parameters for the DWI acquisition is performed for each of the plurality slices or volumes.

15. The method of claim 14, wherein determining the parameters for the DWI acquisition includes selecting a direction of readout, a type of spatial-spectral pulse, or a T1-based fat suppression method.

16. The method of claim 12, wherein selecting the shim parameters includes applying a cost function that optimizes at least one of shim parameters or acquisition parameters on a slice-by-slice or volume-by-volume basis.

17. The method of claim 12, wherein performing the DWI acquisition includes performing a echo-planar imaging (EPI) pulse sequence.

18. The method of claim 12, further comprises selecting a parameter selection function to use to select the shim parameters or acquisition parameters for each of a plurality slices or volumes to be imaged during the DWI acquisition based on a region of the subject being imaged.

19. The method of claim 12, wherein performing the DWI acquisition using the shim parameters also includes dynamically adjusting the shim parameters for each slice or volume.

20. A method for acquiring diffusion weighted imaging (DWI) images of a subject using a magnetic resonance imaging system, the method comprising:
performing a chemical shift encoded pre-scan of the subject to acquire CSE data;
using the CSE data, predicting a water signal and a fat signal across a plurality slices or volumes and select at least one of shim parameters or acquisition parameters for each of the plurality slices or volumes that achieves a desired predicted water signal and fat signal;
performing a diffusion-weighted imaging (DWI) acquisition to acquire DWI data using each of the at least one of shim parameters or acquisition parameters for each of the plurality slices or volumes that achieves the desired predicted water signal and fat signal; and
reconstructing the DWI data to produce an image of the subject with suppressed artifacts induced by fat of the subject.

21. The method of claim 20, wherein performing the DWI acquisition using each of the at least one of shim parameters or acquisition parameters includes dynamically adjusting the at least one of shim parameters or acquisition parameters for each of the plurality slices or volumes.

22. The method of claim 20, wherein selecting at least one of shim parameters or acquisition parameters for each of the plurality slices or volumes includes applying a cost function that optimizes at least one of shim parameters or acquisition parameters on a slice-by-slice or volume-by-volume basis.

* * * * *

UNITED STATES PATENT AND TRADEMARK OFFICE
CERTIFICATE OF CORRECTION

PATENT NO. : 12,411,195 B2
APPLICATION NO. : 18/098539
DATED : September 9, 2025
INVENTOR(S) : Diego Hernando Arribas et al.

It is certified that error appears in the above-identified patent and that said Letters Patent is hereby corrected as shown below:

In the Specification

Column 6, Line 63, "A" should be --Δ--.

Signed and Sealed this
Twenty-fifth Day of November, 2025

John A. Squires
*Director of the United States Patent and Trademark Office*